United States Patent [19]

Testa

[11] Patent Number: 4,615,877

[45] Date of Patent: Oct. 7, 1986

[54] METHOD OF DETERMINING THE OXIDIZING ACTIVITY OF A BIOLOGICAL LIQUID, AND A CORRESPONDING REAGENT

[75] Inventor: Michele Testa, Naples, Italy

[73] Assignee: Savapa S.r.l., Naples, Italy

[21] Appl. No.: 583,859

[22] Filed: Feb. 27, 1984

[51] Int. Cl.$^4$ ............................................. G01N 33/48
[52] U.S. Cl. ......................................... 424/2; 424/9; 424/95; 435/4; 435/29; 436/63
[58] Field of Search ..................... 424/9, 2, 95; 435/4, 435/29; 436/63

[56] References Cited

U.S. PATENT DOCUMENTS

| 4,390,620 | 6/1983 | Junter et al. | 435/29 |
| 4,477,435 | 10/1984 | Courtois et al. | 424/95 |

OTHER PUBLICATIONS

Takemoto et al., Chemical Abstracts, vol. 96 (1982) #197501a.
Iijima et al., Chemical Abstracts; vol. 95 (1981) #183363z.
Ohrloff et al., Chemical Abstracts, vol. 100 (1984) #83737c.

*Primary Examiner*—Christine M. Nucker
*Attorney, Agent, or Firm*—Birch, Stewart, Kolasch & Birch

[57] ABSTRACT

A method of determining the oxidizing capacity of a biological liquid (BLOA) which comprises forming the biological liquid into two samples, incubating one of the two samples at a temperature of 10° C. to 40° C. for a period of 4 to 20 hours, treating each of the samples with a reagent made by homogenizing the lenses of mammals, and measuring and comparing the light absorption of the incubated sample and non-incubated reference sample.

8 Claims, No Drawings

METHOD OF DETERMINING THE OXIDIZING ACTIVITY OF A BIOLOGICAL LIQUID, AND A CORRESPONDING REAGENT

The present invention relates to a method of determining the oxidizing activity of a biological liquid hereinafter (BLOA).

The term "oxidizing activity" used in the present specification means the reduction in the content of —SH groups bonded to the proteins and brought about by substances presented in biological liquids.

The term "biological liquid" means blood, serum or external gland secretions such as saliva or tears.

The invention also relates to a method of preparing the reagent for use in the aforementioned determination, and the corresponding product obtained.

The invention also relates to a method of determining the potential therapeutic activity of a pharmaceutical composition on the oxidizing activity of BLOA from the patient to whom the pharamaceutical composition has been administered.

Other subjects of the invention will be clear from the following specification.

In recent years, many research workers have concentrated their work and observations on the quantity of —SH (sulphhydryl) groups present in the blood, the serum and in biological liquids or tissues in general.

More particularly, the applicant has co-operated with other research workers (Experimental Eye Research, pages 276–290, volume 7, 1968) in publishing a study of the oxidation effect of the —SH groups in proteins presented in lenses, using an amperometric measuring system.

Other authors have studied methods of determining sulphhydryl groups in blood and serum. One particularly interesting published study is the analytical system proposed by G. Ellman and H. Lysko (Analytical Biochemistry, Volume 93, pages 98–102, 1979) where use is made of 5–5'-dithiobis-(2-nitrobenzoic) acid (hereinafter DNBT), N-ethyl maleimide (hereinafter NEM) and nitrothiobenzoate (hereinafter NTB).

This method is v ery accurate but requires skilful handling of samples and very close attention to the perform ce of the various operations.

In view of the importance of determining the aforementioned-SH groups, there is still an urgent problem of obtaining a simple, accurate method of determination which is suitable research instrument at the disposal of research workers.

The applicant has now found a very simple method of determination based on the use of a reagent based on homogenized lenses of mammals.

Accordingly, one essential feature of the invention is the preparation of the aforementioned reagent and use thereof for determining the oxidizing activity of the BLOA.

The present invention is based on the finding that the biological liquids have an oxidizing activity BLOA due to as yet unidentified substances present therein, capable of oxidizing the —SH groups presented in the soluble proteins in the lenses of mammals.

Accordingly, a homogenate is prepared from the aforementioned lenses and used as a specific reagent for determining the oxidizing activity of BLOA.

The lens homogenate is prepared by taking the eyes of mammals within an hour after slaughtering, removing the capsules and epithelial tissues, and homogenizing the residue with a buffer solution at a pH between 7 and 9 at a temperature below 10° C., preferably near 0° C. The preferred buffer solution is a 0.05 N aqueous solution of 2-amino-2-hydroxymethylpropane-1,3 diol hydrochloride (TRIS).

The buffer solution is stablized against bacterial growth by additing a small quantity of sodium azide, normally 0.01 to 0.05% by weight of the solution. The resulting homogenate is clarified by centrifuging any materials in suspension and then dialysed in conventional dialysis tubes, the dialysing solution used being the same buffer solution as used for homogenization plus small quantities of thymol, normally from 100 to 1 000 ppm.

The dialysis operation is performed at a temperature below 10° C., preferably near 0° C., the dialysing solution being repeatedly changed until non-protein —SH groups disappear from the homogenate which has been dialysed (dialysed homogenate).

The disappearance of non-protein —SH groups from the dialysed homogenate is checked by determining the —SH groups in the upper liquid layer of a sample of homogenised dialysate treated with a concentrated aqueous solution of trichloroacetic acid, using the colorimetric reaction with DNTE and NEM.

The dialysis operation normally lasts 36 to 50 hours and the dialyzing solution is changed three times. In this manner, the homogenate is freed from all all low-molecular weight substances soluble in the buffer solution, including those containing —SH groups and capable of reducing accuracy during the subsequent use of the homogenate as a reactant.

The reactive homogenate is then ready for use and is preserved unchanged in vitro at a temperature below $-15°$ C. or is freeze-dried by the normal methods of freeze-drying proteins, after inorganic salts have been eliminated by dialysis with water.

If preserved unchanged at low temperature, the reagent remains active for at least 2 months, whereas it can be used after a year if freeze-dried.

The homogenate can be prepared by using crystal lenses from mammals. The mammals preferred for the purpose according to the invention are bovines, rabbits and mice, in view of the ease with which they are obtainable at slaughterhouses supplying food for human consumption or at biological research laboratories.

Of course, the reagent according to the invention can also be prepared by using the eyes of other mammals provided they are mammals.

In the typical embodiment of the invention, the homogenate prepared as described hereinbefore is used as a reagent by mixing it with the substance to be examined, i.e. the biological liquid, in the following manner:

A small quantity of homogenate, usually a few microlitres, is mixed with the biological liquid to be examined, normally in the ratio of 1 to 4 by volume, and incubated at a temperature of 10° C. to 40° C. for a time between 4 and 20 hours, after which a few ml of DTNB are added, the test-tube is left for 15 minutes at ambient temperature, and a colorimetric reading is obtained of the absorption of light at 410 nm (or a comparison is made with a previously-prepared colour scale). Next, a few microlitres of NEM are added and the colorimetric reading is repeated after 20 minutes.

The difference between the two readings represents the content of —SH groups in the sample. The same procedure is repeated for a similar sample which has not been incubated, thus giving a reference value.

The percentage difference between the reading for the incubated sample and the non-incubated sample represents the oxidizing capacity of the under test BLOA.

In view of the availability of the aforementioned method and the great ease of application thereof, the applicant has been able to make a detailed study of interaction between the oxidizing capacity of the BLOA and a very widespread eye disease—cataract. The pathogenesis of cataract in man is at present attributed to three mechanisms which have been well documented by many research workers—i.e. a change in the impermeability of the lens membrane, denaturing of the lens proteins and oxidation thereof to form insoluble aggregates.

Accordingly there has recently been a series of studies and research activity with the object of treating cataract with drugs having an anti-oxidizing effect on the —SH groups of the proteins, so as to counteract the denaturing of the proteins and stabilize the membranes.

Recently (THE LANCET—Apr. 10, 1982, pages 849-50) the applicant and others have published a pilot study on the use of Bendazac for treating cataract. Enormous interest in this sector has been aroused by the possibility of treating cataract at a very advanced stage and of obtaining remission of incipient sub-capsular cataract.

Initially it was supposed that Bendazac was active because of its attested strong anti-denaturing effect on proteins.

The applicant carried out research on the subject, directing his attention to drugs having similar properties, i.e. anti-inflammatory non-steroid drugs (AINS).

The applicant thus discovered from his own research that there is a correlation between cataract and the oxidizing acitivty of BLOA determined as described by the method according to the invention. He has thus ascertained that AINS drugs have a positive effect in the treatment of cataract, more particularly progressive cataract, but only if they are capable of reducing the oxidizing activity of the BLOA when administered to the patient.

It is thought that the inactivity of AINS which do not reduce the oxidizing activity of BLOA is due to metabolic reasons or to other substances or drugs acting on the liver (formation of active metabolites) or on the receptor, i.e. lenses effected by cataract (opposing competitive effects).

These mechanisms can therefore explain how some AINS are less than 50% effective on patients suffering from metabolic diseases such as diabetes or being simultaneously treated with other drugs, more particularly with psychotropic drugs, or who have particular eye conditions such as severe myopia or glaucoma.

Accordingly, in evaluating the possibility of treating cataract, it is essential to have a test for determining beforehand whether the drug selected for treatment has a curative capacity. This test is an essential feature of the invention.

The test is very simple and consists in treating the patient under examination with the drug which is assumed to be of use in the treatment of cataract and in measuring the variation in oxidizing activity of BLOA in the patient before and after administration of the drug, using the method of measurement described in the first part of the specification.

The drug is administered to the patient in the normal commercial form and in the minimal quantity described in the normal dosage given in the instructions accompanying the packaging.

Two hours after administering the drug, a sample of biological liquid is taken from the patient and used to measure the BLOA. If the BLOA has decreased, the drug is potentially active in the treatment of cataract, whereas if the BOA has not changed, the drug has no effect in the treatment of cataract.

It is thus possible, by testing various types of drug, to select the drug suitable for treating the patient under examination, so that treatment can be selective, based on the individual response of each patient to drug treatment.

The therapeutic importance of this procedure is clear, since it supplies the physician with an irreplaceable facility for treating a disease as complex and widespread as cataract.

It has thus been found that reactions to a given drug vary considerably from one patient to another and that only patients which are "responsive", i.e. patients in which the aforementioned tests have shown a reduction in BLOA resulting from treatment with the drug, will show improvements in cataract resulting from therapeutic treatment with the aforementioned drug.

It has therefore been found in a completely unexpected surprising manner that the anti-inflammatory power of AINS drugs is not related to their action against cataract and that some drugs having low anti-inflammatory power are much more effective in the treatment of cataract than other similar drugs having anti-inflammatory power.

The following examples will illustrate the invention some clearly without in any way limiting its scope:

EXAMPLE 1

50 calves' eyes were taken immediately after they have been slaughtered. As soon as they had been removed, the eyes were immersed in a mixture of ice and water and brought to the laboratory, where the lenses were taken out and freed from the capsules.

After being taken out of the capsules, the lenses were homogenized in a Potter-Elvehejm-type glass homogenizer immersed in a bath maintained at 0° C. and mixed with 125 ml of a 0.05 M aqueous buffer solution of TRIS containing 0.03% sodium azide at pH 8.2.

The homogenate was then centrifuged at 6 000 rpm for 30 minutes to ensure the complete elimination of any insoluble material, taking care to keep the temperature always below 10° C.

After being thus clarified, the homogenate was placed in a collodion dialysis tube and the homogenate was dialysed by the buffer solution used for homogenization after adding 50 ppm thymol as a bacteriostatic.

Dialysis was performed at 5° C. using 2 liters of buffer solution, which was renewed every 12 hours.

After the buffer solution has been replaced for the third time, a samll sample of homogenate was taken and treated with 50% trichloroacetic acid, the absence of non-protein —SH groups being confirmed by colorimetric reaction between DTMN and NEM and the supernatant layer of liquid.

The protein concentration of the resulting dialysed homogenate, measured by the Warburg and Christian method, was found to be 17.6%.

The homogenate was then transferred from the dialysis tube to a glass container and preserved at −20° C.

EXAMPLE 2

The procedure described in the Example 1 was repeated, the method of operation being the same, using 10 rabbit's eyes.

The lenses were homogenized with 5 ml of buffer solution at each renewal.

The resulting dialysed homogenate had a protein concentration of 18%.

EXAMPLE 3

The procedure described in Example 1 was repeated, the method of operation being the same, using 60 mouse's eyes.

The lenses were homogenized with 5 ml buffer solution and dialysed with 80 ml buffer solution at each renewal. The resulting dialysed homogenate had a protein concentration of 17.2%.

EXAMPLE 4

A portion of dialysed homogenate obtained as described in Example 1 was diluted with the same buffer solution as used for homogenization, until the protein content was 3 mg/ml.

8 microlitres of the dilute homogenate were mixed with 42 microlitres of serum (clear and not haemolysed, obtained by simple coagulation of a blood sample) mixing being carried out immediately in a plastics cell for spectrometric measurements.

The cell was closed and incubated at 35° C. for 4 hours. After incubation, 2 ml DTNB were introduced into the cell and a first measurement of light absorption was made by the Ellman and Lysko method using a Beckmann spectrophotometer. Next, 20 microliters of NEM were added to the cell contents and another colorimetric reading was made, the difference between the two values being recorded as the absorption value of the sample. The operations and readings were repeated on a sample of homogenate mixed with serum but without incubating the mixture.

The percentage difference between the absorption of the non-incubated and the incubated sample was found to be 33.3%. This represents the oxidizing activity of the serum of the patient under examination (BLOA).

In a repeat of the entire procedure describe, a sample of serum from the same patient was examined after being obtained from a blood sample taken two hours after administration of 0.2 g butazolidine, the BLOA value being found equal to 20.

It was thus shown that the patient responded positively to treatment with the butazolidine drug.

In the event, the patient was treated with butazolidine for 15 days and showed a marked improvement in correct vision occular refraction and trasparency of the lens. The entire procedure described hereinbefore for determining the BLOA of the patient was repeated in parallel, using the patient's saliva as biological liquid instead of serum.

The measured BLOA value and the variation therein resulting from administration of the drug were found to be completely similar to those obtained with serum.

EXAMPLE 5

A clinical test was made on 41 male patients aged between 40 and 65, suffering from central posterior subcapsular idiopathic catarct.

The patients examined during the research did not have any metabolic diseases or serious eye defects and were not treated with drugs different from those given during the observation period.

The BLOA values for all the patients under examination were measured (either on the serum or saliva) and found to be between 10 and 32, using the procedure described in Example 4.

The BLOA values for the same patients were also determined two hours after administering the following drugs: Bendalina made by Messrs. Acraf, Froben by Boots-Formenti and Tantum by ACRAF using the minimum does and following the procedure indicated on the commercial packaging.

The measured descrease in BLOA values was significant (i.e. more than 30% below the originally measured value) in 7 patients treated with Bendalina, 14 treated with Froben and 11 treated with Tantum, whereas 9 patients showed no decrease in BLOA after administration of any of the three drugs under examination.

This was followed by therapeutic treatment for 20 days, each patient being given the drug which had produced the greatest decrease in BLOA in the test.

The 9 patients who had shown no reduction in BLOA after any of the three tested drugs were treated with one of the three available drugs in a random manner, three patients for each drug.

At the end of treatment, there was a marked improvement in correct vision, refraction and transparency of the lens in 5 out of 7 patients treated with Bendalina, 7 out of 17 patients treated with Froben and 8 out of 11 patients treated with Tantum, whereas none of the 9 patients who had not shown a reduction in BLOA in the preliminary test showed visible signs of improvement.

I claim:

1. A method of determining the oxidizing capacity of a biological liquid (BLOA) which comprises the steps of:

forming the biological liquid into two samples,
   incubating one of the two samples at a temperature of 10° C. to 40° C. for a period of 4 to 20 hours,
   treating each of the samples with a reagent made by homogenizing the lenses of mammals, and
   measuring and comparing the light absorption of the incubated sample and non-incubated reference sample.

2. The method as claimed in claim 1 the homogenate is of lenses from calves.

3. The method as claimed in claim 1 the homogenate is of lenses of rabbits.

4. The method as claimed in claim 1 the homogenate is of lenses of mice.

5. The method as claimed in claim 1 incubation is performed at a temperature of 32° C. to 35° C. for a period of 4 hours.

6. A method for evaluating the potential therapeutic activity of a drug used in the treatment of cataracts which comprise the steps of:

taking a first sample of biological liquid from the patient and determining the oxidizing capacity thereof according to claim 1,
   administering the drug to the patient,
   taking a second sample of a biological liquid from the patient and determining the oxidizing capacity thereof according to claim 1, and
   evaluating the therapeutic activity of the drug by measuring the relation in the oxidizing activity of the respective samples of biological liquid.

7. The method for evaluating the potential therapeutic activity of the drug of claim 6 wherein the drug is administered in the minimum quantity prescribed in the normal dosage.

8. The method for evaluating the potential therapeutic activity of a drug used in the treatment of cataracts of claim 6 wherein the second sample is taken two hours after administration of the drug.

* * * * *